United States Patent [19]

Flowers et al.

[11] Patent Number: 5,364,767
[45] Date of Patent: Nov. 15, 1994

[54] CHROMOGENIC COMPOUNDS AND METHODS OF USING SAME

[75] Inventors: Daniel G. Flowers, Cuyahoga Falls; Marvin Sternfeld, Pepper Pike, both of Ohio

[73] Assignee: Research Organics, In., Cleveland, Ohio

[21] Appl. No.: 16,511

[22] Filed: Feb. 11, 1993

[51] Int. Cl.$^5$ .......... C12Q 1/06; C12Q 1/04; C12Q 1/54; C07H 15/00
[52] U.S. Cl. .......... 435/39; 435/34; 435/29; 435/25; 435/19; 435/14; 435/4; 435/21; 435/18; 536/17.2; 536/4.1; 536/17.5; 536/17.4
[58] Field of Search .......... 435/39, 14, 18, 19, 435/21, 34, 25, 29, 4; 536/4.1, 17.3, 17.5, 17.2, 24

[56] References Cited

U.S. PATENT DOCUMENTS

| | | | |
|---|---|---|---|
| 3,496,066 | 2/1970 | Berger et al. | 435/39 |
| 3,679,672 | 7/1972 | Yamamoto et al. | 544/143 |
| 3,870,601 | 3/1975 | Warren et al. | 435/39 |
| 3,886,165 | 5/1975 | Wu et al. | 546/101 |
| 3,936,356 | 2/1976 | Janin | 435/39 |
| 4,351,823 | 9/1982 | Rubin | 424/9 |
| 4,556,636 | 12/1985 | Belly et al. | 435/34 |
| 4,591,554 | 5/1986 | Koumura | 435/18 |
| 4,603,108 | 7/1986 | Bascomb | 435/34 |
| 4,617,309 | 10/1986 | Böttcher et al. | 546/270 |
| 4,673,638 | 6/1987 | Grosch et al. | 435/34 |
| 4,795,736 | 1/1989 | Hung et al. | 428/913 |
| 4,946,776 | 8/1990 | Ritterband | 435/4 |
| 5,079,165 | 1/1992 | Clements et al. | 536/27 |

OTHER PUBLICATIONS

Wolf et al, "American Journal of Clinical Pathology", vol. 44, No. 3, pp. 307–314, 1965.
Piper et al, "J. Organic Chem.", vol. 27, pp. 3134–3137; 1962.
Watkins et al, Applied & Environmental Microbiology, Jul. 1988, pp. 1874–1875.
Holt et al, Molecular Association & Structure in Indigoid Dyes, pp. 495–505 (1958).
Manafi et al (Abstract)(1989) Zentralbl Hyg Unweltmed 189(3).
Ley et al, Can. J. Microbiol., 34:690–693 (1987).
Manafi, M; Kneifel,. W, Umweltmed, Zentralbl Hyg, 189(3), 1989, 225–234, A. Combined Chromogenic-Fluorogenic Medium for the Simultaneous Detection of Total Coliforms and E. coli in Water.
Holt, S. J. et al, Studies in Enzyme Cytochemistry III: Relationships Between Solubility, Molecular Association and Structure in Indigoid Dyes, pp. 495–505 (1958).

(List continued on next page.)

Primary Examiner—Michael G. Wityshyn
Assistant Examiner—Louise N. Leary
Attorney, Agent, or Firm—Renner, Otto, Boisselle & Sklar

[57] ABSTRACT

The present invention relates to chromogenic compounds which are represented by the general Formula (I):

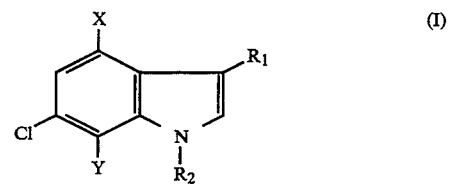

wherein $R_1$ is a sugar group, ester group, hydrocarbyl group, phosphate group, sulfate group or a salt thereof, with the proviso that $R_1$ is other than $\beta$-D-glucuronic acid or $\beta$-D-galactopyranoside, $R_2$ is H or hydrocarbyl group containing 1 to about 5 carbon atoms, X is Cl or H, and Y is Cl or H. The present invention further relates to a method for quantitatively identifying and differentiating a first biological material having enzyme specificity for a first chromogenic compound as represented by Formula (I) above, and a second biological material having enzyme specificity for a second chromogenic compound.

26 Claims, No Drawings

OTHER PUBLICATIONS

Epstein, E. et al, An Indigogenic Reaction For Alkaline Phosphatase in Disk Electrophoresis, Am. J. Clin. Path. vol. 48, No. 5, pp. 530–534, 1967.

Pearson, B. et al, Histochemical B-Glucuronidase Distribution in Mammalian Tissue as Detected by 5–Bromo-4-Chloro-3-yl-β-D-Glucopyruroniside, Lab. Invest., vol. 17, No. 2, pp. 217–223, 1967.

Jefferson, R. A. et al, β-Glucuronidase from *E. coli*, as a gene-fusion marker, Proc. Natl. Acad. Sci. USA, vol. 83, pp. 8447–8451, 1986.

Delisle, G. J. et al, Rapid Detection of *E. coli* in Urine Samples by a New Chromogenic β-Glucuronidase Assay, J. Clin. Microbiol., vol. 27, No. 4, pp. 778–779, 1989.

Wolf, P. L. et al, The Utilization of the Indigogenic Reaction for the Demonstration of N-Acetyl-β-Glucosaminidase, Amer. J. Clin. Path., vol. 44, No. 3, pp. 307–314, 1965.

Lin, W. et al, Development of Micrometastases: Earliest Events Detected with Bacterial Lacz Gene-Tagged Tumor Cells, J. Nat'l. Cancer Inst., vol. 82, No. 18, pp. 1497–1502, 1990.

Lin W., et al, Selectable Plasmid Vectors with Alternative and Ultrasensitive Histrochemical Marker Genes, Biotechniques; vol. 11, No. 3, pp. 344–351, 1991.

Tsou, K. C. et al, Indigogenic Phosphodiesters as Potential Chromogenic Cancer Chemotherapeutic Agents, J. Med. Chem., 15, 1221 (1972).

Jefferson, R. A., GUS Fusions: β-glucuronidase as a Sensitive and Versitile Gene Fusion Marker in Higher Plants, EMBOJ., vol. 6, No. 13, pp. 3901–3907, 1987.

Holt, S. J. et al, Studies in Enzyme Cytochemistry II: Synthesis of Indigogenic Substrates for Esterases, Proc. Roy. Soc., vol. 148B, pp. 481–494, 1958.

Holt, S. J. Indigogenic Staining Methods for Esterases, in General Cytochemical Methods, J. F. Danielli, Ed., Academic Press, NY, N.Y. pp. 375–397, 1958.

Piper, J. R. et al, Substituted Indole-3-Acetic Acids by the Reformatsky Reaction, J. Org. Chem., vol. 27, pp. 3134–3137, 1962.

Sadler, P. W. et al, Synthesis and Absorption Spectra of the Symmetrical Chloroindigos, J. Amer. Chem. Soc. vol. 78, pp. 1251–1255, 1956.

Holt, S. J. et al, Vibrational Frequency Correlations in Hetero–cyclic Molecules Part IV. Indoxyl Derivatives, J. Chem. Soc., pp. 1217, 1958.

Horowitz, J. P. et al, Substrates for Cytochemical Demostration of Enzyme Activity I. Some Substituted 3-indolyl-β-D-glycopyranosides J. Med. Chem., vol. 7, No. 4, pp. 574–575, 1964.

Ausubel, F. M. et al, Short Protocols in Molecular Biology 2ed, Greene Publishing Associates and John Wiley and Sons., New York (1992), Ch. 11:Immunology pp. 11–1 to 11–15.

Zollinger, H.; Color Chemistry: Synthesis, Properties and Applications of Organic Dyes and Pigments 2ed., VCH Publishers, New York, Ch. 8.3: Indigo and its Derivatives, pp. 191–199.

CHROMOGENIC COMPOUNDS AND METHODS OF USING SAME

FIELD OF THE INVENTION

The present invention relates to chromogenic compounds and methods of using same. More particularly, the present invention relates to chromogenic compounds which are chlorine substituted 3-indolyl derivatives. The chromogenic chlorine substituted 3-indolyl derivatives are useful in the fields of biotechnology, diagnostic chemistry, microbiology, molecular biology and the like.

BACKGROUND OF THE INVENTION

Chromogenic compounds are indicative compounds capable of producing color by causing a displacement of, or the appearance of, absorbent bands in the visible spectrum. Indicative compounds are useful because they have significant applications in the fields of biotechnology, diagnostic chemistry, microbiology, molecular biology and the like.

Indicative compounds are, among other things, particularly useful in the identification of biological material such as genetically transfected cells and organisms. Their employment in cloning vectors, which are used to create genetically engineered cells and organisms, is well known. Specifically, a histochemical marker gene may be incorporated into a cloning vector in order to subsequently identify successful transfectants. A successful transfectant carries both the desired gene and the histochemical marker gene. The marker gene may be induced to express a marker gene product in the form of a marker enzyme. Thereafter, a chromogenic compound may be used to detect the presence of a particular marker enzyme by generating distinct colored reaction products as a result of enzymatic activity.

Likewise, the use of multiple histochemical marker genes, which generate different color reaction products, would facilitate the analysis of multiple cell populations. In particular, the use of multiple histochemical marker genes permits the distinction between two or more cell types possessing histochemically different marker genes. Thus, it is desirable to develop techniques wherein transfectants, which carry different histochemical marker genes, may be distinguished from each other.

Indicative compounds are also useful with regard to locating a specific sequence of DNA or RNA. In particular, specific sequences of DNA or RNA may be located on chromosomes or other genetic material with the use of nucleic acid probes. Nucleic acid probes contain short segments of nucleic acids which are complimentary to the specific DNA or RNA sequence to be located. Currently, it is well known to prepare nucleic acid probes containing radioactive isotopes, i.e., of phosphorus, in order to subsequently identify and locate the nucleic acid probe on a chromosome or on other genetic material. Therefore, for environmental and safety reasons, it is desirable to develop alternative, non-isotopic techniques which locate and identify nucleic acid probes in order to eliminate the use of dangerous radioactive materials.

Furthermore, indicative compounds are useful when used in conjunction with enzyme-antibody conjugates. Enzyme-antibody conjugates are important with respect to enzyme linked immunosorbent assays. In this regard, enzymes are conjugated with antigen specific antibodies which permit detection of a particular antigen. Thus, in order to facilitate the detection of a particular antigen, it is desirable to improve methods which utilize enzyme-antibody conjugates, such as immunoblotting techniques.

In microbiology, the presence of indicator organisms is frequently used to determine the quality of various products. For example, in the analysis of water, food and dairy products, the presence of members of the "coliform" group as well as the presence of the bacterial species Escherichia coli (E. coli) are considered very significant quality indicators. Numerous methods for determining, identifying and enumerating indicator organisms currently exist, with varying degrees of accuracy and facility. Some test methods merely indicate the presence or absence of the organisms whereas other methods attempt to quantify the organisms in the test materials.

For instance, the reagent 5-bromo-4-chloro-3-indolyl-$\beta$-D-galactopyranoside (X-Gal) is a known test compound for identifying coliforms. When acted on by the $\beta$-galactosidase enzyme produced by coliforms, X-Gal forms an insoluble indigo blue precipitate. X-Gal can be incorporated into a nutrient medium such as an agar plate, and if a sample containing coliforms is present, the coliforms will grow as indigo blue colonies. Since X-Gal forms an insoluble precipitate, rather than a diffusible compound, X-Gal allows the quantitative determination of coliforms.

Recently, a similar compound, 5-bromo-4-chloro-3-indolyl-$\beta$-D-glucuronic acid (X-Gluc) has been developed for the identification of E. coli. When acted on by the $\beta$-glucuronidase enzyme produced by E. coli, X-Gluc forms an insoluble indigo blue precipitate. Since X-Gluc forms an insoluble precipitate, 15 rather than a diffusible compound, X-Gluc allows the quantitative determination of E. coli. Further, it does not require the use of ultraviolet light. X-Gluc and its ability to identify E. coli are described in Watkins, et al, Appl. Environ. Microbiol. 54:1874–1875 (1988). A similar compound, indoxyl-$\beta$-D-glucuronide, which also produces sharp blue colonies of E. coli, was described in Ley, et al, Can. J. Microbiol. 34:690–693 (1987).

X-Gal and X-Gluc have the disadvantage that they each contain the exact same chromogen and therefore the two cannot be used together to identify and distinguish between both E. coli and general coliforms in a single test with a single sample. The two indicator compounds cannot be used together because both X-Gal and X-Gluc generate the formation of identically hued indigo blue colonies. On one hand, a person using both reagents together would be able to quantitatively identify the total number of coliforms, however; on the other hand, the reagents would not be able to indicate which of the colonies were E. coli and which were other coliforms besides E. coli. Therefore, it is desirable to develop novel indicator compounds which can identify and enumerate indicator organisms when used alone and in combination with other indicator compounds.

Accordingly, it is clear from the foregoing that improved methods to effectively quantify, identify and/or differentiate biological material such as microorganisms, transfectants, antigens, DNA or RNA sequences and the like are needed, and there is a continuing search for better, more accurate, simpler and varied methods in these areas.

SUMMARY OF THE INVENTION

The present invention relates to chromogenic compounds which are represented by the general Formula (I):

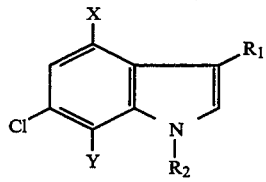

wherein $R_1$ is a sugar group, ester group, hydrocarbyl group, phosphate group, sulfate group or a salt thereof, with the proviso that $R_1$ is other than β-D-glucuronic acid or β-D-galactopyranoside, $R_2$ is H or hydrocarbyl group containing 1 to about 5 carbon atoms, X is Cl or H, and Y is Cl or H.

The present invention further relates to a method for quantitatively identifying and differentiating a first biological material having enzyme specificity for a first chromogenic compound as represented by Formula (I) above, and a second biological material having enzyme specificity for a second chromogenic compound, comprising the steps of: combining the first chromogenic compound capable of forming an insoluble precipitate of a first color upon reacting with an enzyme from the first biological material, a second chromogenic compound capable of forming an insoluble precipitate of a second color contrasting with the first color upon reacting with an enzyme from the second biological material, and a nutrient base medium to form a test medium; inoculating the test medium with a sample to be tested for the presence of biological material; incubating the test medium; examining the test medium for the presence of colonies having the first color, such colonies being colonies of the first biological material having enzyme specificity for the first chromogenic compound; and the presence of colonies having the second color, such colonies being colonies of the second biological material having enzyme specificity for the second chromogenic compound; and enumerating the colonies of the first biological material and the colonies of the second biological material.

DETAILED DESCRIPTION OF THE INVENTION

The chromogenic compounds of the present invention are represented by the general Formula (I):

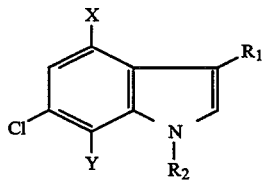

wherein $R_1$ is a sugar group, ester group, hydrocarbyl group, phosphate group, sulfate group or a salt thereof, with the proviso that $R_1$ is other than β-D-glucuronic acid or β-D-galactopyranoside, $R_2$ is H or hydrocarbyl group containing 1 to about 5 carbon atoms, X is Cl or H, and Y is Cl or H.

In one embodiment of the present invention, the chromogenic compounds are represented by Formula (II):

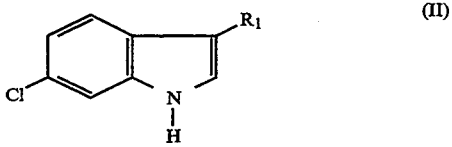

wherein $R_1$ is a sugar group, ester group, hydrocarbyl group, phosphate group, sulfate group or a salt thereof with the proviso that $R_1$ is other than β-D-glucuronic acid or β-D-galactopyranoside.

The chromogenic compounds of the present invention comprise a chlorine substituted 3-indolyl substituent and an $R_1$ group. The $R_1$ group is joined to the chlorine substituted 3-indolyl substituent by an ester or ether linkage. Optionally, the chromogenic compounds may further comprise a hydrocarbyl group, $R_2$ in Formula (I), at the 1 position of the indole molecule. The $R_1$ group is joined at the 3-position of the indole molecule to a substituent which forms an insoluble precipitate of color when liberated by a chemical reaction or by the action of an enzyme having specificity for the particular $R_1$ group. The precipitates may be insoluble in the test medium so that the biological material or reaction medium producing each precipitate may be visually quantified. Further, it will be readily appreciated that the $R_1$ group should include compounds which are approximately colorless, or are not deeply colored, so that they do not interfere with the detection of the colored insoluble precipitates produced by the chemical reaction or the action of an enzyme on the chromogenic compounds of the present invention. The $R_1$ groups should also be compounds that can be made soluble in the selected test medium.

The chromogenic compounds of the present invention comprise a chlorine substituted substituent. The chlorine substituted substituent may contain from one to three chlorine atoms at the 4, 6 and/or 7 positions of the indole molecule. In one embodiment of Formula (I), X is chlorine and Y is hydrogen and the chromogenic compound comprises a 4,6-dichloro-3-indolyl substituent. In another embodiment, Y is chlorine and X is hydrogen and the chromogenic compound comprises a 6,7-dichloro-3-indolyl substituent. In yet another embodiment, X and Y are both chlorine and the chromogenic compound comprises a 4,6,7-trichloro-3-indolyl substituent. In a preferred embodiment, X and Y are both hydrogen and the chromogenic compound comprises a 6-chloro-3-indolyl substituent.

The chromogenic compounds of the present invention may further comprise a hydrogen or hydrocarbyl group, $R_2$ in Formula (I), at the 1 position of the indole molecule. In a preferred embodiment, $R_2$ is hydrogen. Alternatively, $R_2$ may be a hydrocarbyl group containing one to about five carbon atoms. In another preferred embodiment, $R_2$ is a hydrocarbyl group containing two carbon atoms. In yet another preferred embodiment, $R_2$ is $COCH_3$.

In one embodiment of the present invention, $R_1$ is a sugar group. Sugars, for purposes of the present invention are monosaccharides, disaccharides and polysaccharides. In a preferred embodiment of the present invention, the sugar group is a monosaccharide in the ring form. Representative sugar groups include β-D-galactosaminide, β-D-glucopyranoside, β-D-glucosaminide and salts thereof. Sugars which contain acidic functions would include stable salt forms. Suitable salts are derived from bases including alkali metal or alkaline earth metal hydroxides or carbonates, for example, sodium hydroxide, potassium hydroxide, calcium hydroxide, magnesium hydroxide, and corresponding carbonates; and nitrogen bases such as ammonia and alkylamines such as trimethylamine, triethylamine, p-toluidine and cyclohexylamine. Other salts include lithium salts.

In one embodiment of the present invention, $R_1$ is an ester group. The ester group, in a preferred embodiment of the present invention, contains at least about two carbon atoms. In another preferred embodiment, the ester group contains at most about eight carbon atoms. Representative esters include acetate, propionate, butyrate, hexanoate and octanoate (caprylate).

The term "hydrocarbyl" is used herein to include substantially hydrocarbyl groups as well as purely hydrocarbyl groups. The description of these groups as being substantially hydrocarbyl means that they do not contain non-hydrocarbyl substituents or noncarbon atoms which significantly affect the hydrocarbyl characteristics or properties of such groups relevant to their uses as described herein. Examples of hydrocarbyl substituents which might be useful in connection with the present invention include alkyl, alkenyl, alicyclic and aromatic groups.

In one embodiment of the present invention, $R_1$ is a hydrocarbyl group containing at least one carbon atom and less than 10 carbon atoms. The hydrocarbyl group, in a preferred embodiment of the present invention, contains at least about 2 carbon atoms. In another preferred embodiment, the hydrocarbyl group contains at most about 8 carbon atoms.

In one embodiment of the present invention, the $R_1$ group is a phosphate group, sulfate group or a salt thereof. Representative phosphate groups include phosphate, phosphate derivatives, and salts thereof. Representative phosphate derivatives include nucleoside phosphodiesters, nucleoside pyrophosphates, pyrophosphates and salts thereof. Nucleoside phosphodiesters include nucleoside phosphodiester and nucleoside phosphodiester derivatives and salts thereof. Representative sulfate groups include sulfate, sulfate derivatives and salts thereof. Suitable salts include sodium salts, potassium salts, lithium salts, magnesium salts and amine salts such as p-toluidine, cyclohexylammonium and other alkylamines.

The determination of whether a given $R_1$ group is operable within the scope of the present invention involves a simple test. The test involves placing a chlorine substituted 3-indolyl derivative with a given $R_1$ group to be tested in an agar or pectin test medium inoculated with a microorganism which contains an enzyme having specificity for the cleavage of the given $R_1$ group and observing whether colored colonies grow in the test medium. Alternatively, a test may be conducted by placing a chlorine substituted 3-indolyl derivative with a given $R_1$ group to be tested in a suitable test medium which contains a chemical compound with the potential ability to cleave the oxygen linkage and observing whether colored substance appears in the test medium.

Useful embodiments of the chromogenic compounds of the present invention wherein $R_2$ is a hydrocarbyl group include 6-chloro-3-indolyl-N-acetyl-β-3-D-galactosaminide, 6-chloro-3-indolyl-N-acetyl-β-D-glucosaminide, 6-chloro-3-indolyl-1,3-diacetate.

Useful embodiments of the chromogenic compounds of the present invention wherein $R_2$ is hydrogen include: 6-chloro-3-indolyl butyrate, 6-chloro-3-indolyl octanoate, 6-chloro-3-indolyl phosphate p-toluidine salt, 6-chloro-3-indolyl sulfate, 6-chloro-3-indolyl-β-D-glucopyranoside, and 6-chloro-3-indolyl acetate. These compounds produce an insoluble precipitate having an approximate magenta color, contrasting with and visually distinguishable from indigo blue, when developed with an enzyme having specificity for the particular $R_1$ group or a chemical compound with the ability to cleave the oxygen linkage. More specifically, the colors produced by the chromogenic chlorine substituted 3-indolyl derivatives are distinctive in comparison to the colors produced by 5-bromo-4-chloro-3-indolyl-β-D-galactopyranoside-(X-Gal), 5-bromo-4-chloro-3-indolyl-β-D-glucuronicacid(X-Gluc), 5-bromoindoxyl acetate and 5-bromo-4-chloro-3-indolyl phosphate (BCIP), four commonly used chromogenic substrates. An approximate magenta color is intended to include the color magenta and colors similar to magenta. Colors similar to magenta include red, mauve, pink, purple and various shades and mixtures thereof.

The chlorine substituted 3-indolyl derivatives of Formulae (I) and (II) form an insoluble magenta precipitate when reacted upon by a chemical compound with the ability to cleave the oxygen linkage or by an enzyme having specificity for the various $R_1$ groups. Consequently, this color contrasts with the indigo blue precipitate formed as a result of the action of enzyme β-galactosidase on 5-bromo-4-chloro-3-indolyl-β-D-galactopyranoside(X-Gal). The chlorine substituted 3-indolyl derivatives may be used individually or together with other chromogenic compounds known in the art. In this regard, the chromogenic compounds of the present invention are effective for quantifying, identifying and differentiating biological material which contain one or more enzymes having specificity for a particular $R_1$ group. Specifically, the chromogenic compounds of the present invention may be effective for quantifying, identifying and/or differentiating specific enzymes linked to an antibody, nucleic acid probes, affinity proteins, matrixes, antigens, DNA or RNA sequences, transfectants, microorganisms and the like.

As stated above, the unique approximately magenta color produced by the chromogenic compounds of the present invention affords the chromogenic compounds diverse and numerous applications. Generally, the chlorine substituted 3-indolyl derivatives are useful chromogenic enzyme substrates. For instance, in one application involving the identification of genetically transfected cells or organisms, successful transfectants carrying a histochemical marker gene may be induced to produce a corresponding marker enzyme. The marker enzyme may be detected with the use of a chromogenic compound of the present invention. Similarly, successful transfectants carrying different histochemical marker genes may be distinguished when using the chromogenic compounds of the present invention with other chromogenic substrates, such as 5-bromo-4-chloro-3-indolyl-β-D-galactopyranoside (X-Gal). Chromogenic compounds of the present invention may also be utilized for histochemical staining of bacteria, cell cultures, tissue sections and the like.

In one embodiment of the present invention, chromogenic compounds may be used to detect nucleic acid probes. Nucleic acid probes, used to locate specific DNA or RNA sequences, may contain covalently linked enzymes having specificity for a chromogenic compound of the present invention. In a similar application, chromogenic compounds of the present invention may be used to detect nucleic acid probes having a biotin-streptavidin-enzyme complex. In both of these applications, the presence of an enzyme with the requisite specificity linked to the nucleic acid probe enables detection by a chromogenic compound of the present invention.

In one embodiment of the present invention, chromogenic compounds may be used to detect an enzyme-antibody conjugate. The detection of enzyme-antibody conjugates is important because they are utilized in immunoblotting techniques which locate specific antigens.

While not intending to be limited by any theory, it is believed that by a chemical reaction or an enzyme having specificity for the particular $R_1$ group reacts with the chromogenic compound releasing the chlorine substituted 3-indolyl substituent, which, in turn, reacts with itself forming a colored precipitate. Generally, chromogenic compounds of the present invention permit the detection of specific enzymes linked to, or present in antibodies, antigens, nucleic acid probes, affinity proteins, matrixes, DNA or RNA sequences, transfectants, microorganisms and the like.

The following is an example of the preparation of a typical reagent for the staining of cell cultures, tissues and organisms. A solution of alcohol/water is prepared which contains 1.0–2.0 mg/ml of a chromogenic compound, 5–20 mM potassium ferricyanide, 5–20 mM potassium ferrocyanide and 2 mM magnesium chloride. The alcohol/water ratio may vary depending upon the characteristics of the particular chromogenic compound added to the solution.

The preparation of reagent for other applications, such as the staining of bacterial cultures, requires a solution of DMF, DMSO or THF containing 1–10 mg/ml of the chromogenic compound. Direct use of the reagent as a histochemical stain is possible.

The following is a more specific example of the preparation of a common test medium suitable for 6-chloro-3-indolyl esters of the present invention. An oxidant containing 0.05M potassium ferricyanide and 0.05M potassium ferrocyanide is prepared. A 6-chloro-3-indolyl ester is dissolved as 1–2 mg in 0.1 ml of ethanol. The dissolved chromogenic compound is added to 2.0 ml of 0.1M Tris/Tris HCl buffer, pH=8.5. To this solution is added 1.0 ml of 1M $CaCl_2$ and 5.0 ml of 2M NaCl. The chromogenic compound solution is brought to a final volume of 10 ml with distilled water. This chromogenic compound reagent solution should be prepared just prior to use.

This chromogenic compound reagent solution is basically the same for all of the chlorine substituted 3-indolyl derivatives. Once prepared, the reagent is applied to the test sample such as a plated bacterial culture or tissue culture. The sample is allowed to incubate for an amount of time which allows appropriate color development.

In the chromogenic compound reagent solution dimethylformamide or dimethylsulfoxide may be substituted in place of ethanol in order to dissolve the chromogenic compound. The reagent buffer compounds may also be changed to achieve a different pH. This is common for the use of the phosphate $R_1$ group for alkaline phosphatase analysis which is most active in a pH range of about 8 to about 10.

The following Examples A to D illustrate the preparation of 6-chloro-3-indolyl precursors.

EXAMPLE A 4-chloroanthranilic acid

To a solution of 70.8 g (0.5M) 5-chloro-2-methylaniline in 70 ml glacial acetic acid is added with 52 g (0.51M) acetic anhydride and brought to gentle reflux for 30 minutes. The solution is poured into 400 ml cold water and the N-acetyl-5-chloro-2-methylaniline that separates is filtered off and washed with cold water.

The damp acetyl derivative is suspended in 2 liters of 0.25M magnesium sulfate solution at 85° C. With vigorous stirring, 240 g potassium permanganate is added, portionwise, over a 1.5 hour period, keeping the temperature between 85° C. and 90° C. The mixture is filtered hot, and the manganese dioxide by-product is washed with 1 liter of hot water. The aqueous flitrate is cooled to room temperature and acidified with 20% sulfuric acid to a pH of about 1, precipitating N-acetyl-4-chloroanthranilic acid. The product is recovered by filtration and washed with cold water.

The damp N-acetyl-4-chloroanthranilic acid is suspended in 400 ml of concentrated hydrochloric acid (12M) and stirred and heated at 80° C. for 8 hours. The mixture is cooled to 10° C. and the resulting 4-chloroanthranilic acid hydrochloride is recovered by filtration. The solid is suspended in 300 ml water and sodium acetate is added, portionwise until the pH is 5. The resulting 4-chloroanthranilic acid is recovered by filtration and recrystallized from the minimum of hot ethanol. The final yield of off-white crystals was about 50 g, melting at about 239°–240° C.

EXAMPLE B 5-chloro-2-carboxyphenylglycine sodium salt

4-Chloroanthranilic acid weighing 474 g (2.69M) is suspended in 1200 ml water in a 5 liter flask. A 30% potassium hydroxide solution is added, slowly, with stirring, until the pH is in the range of 7.0 to 8.0. The 4-chloroanthranilic acid dissolves to form a solution of the potassium salt. To this solution is added a solution of 326.5 g (2.80M) of sodium monochloracetate in 800 ml water. The resulting solution is then placed in a pressure bottle and allowed to stand at 60° C. for three days. The product precipitates and the mixture is almost solid after three days. The product is recovered by filtration and washed with 200 ml ice cold water. After drying in vacuo, the off white product weighed about 335 g (43% yield) and melted at about 278°–280° C.

EXAMPLE C 6-chloroindoxyl-1,3-diacetate

Into a 5 liter, 3-neck flask equipped with mechanical stirring, reflux condenser and gas evolution bubbler is placed 335 g (1.33M) of 5-chloro-2-carboxyphenylglycine sodium salt, 2.3 liters acetic anhydride and 421 g of anhydrous sodium acetate. The mixture is brought to reflux and maintained for 3 hours until the evolution of carbon dioxide is nearly complete. The mixture is placed in a beaker while hot and chilled to 0° C. overnight. The next day the product is recovered by filtration and mixed with 2 liters water and stirred for 1 hour to hydrolyze any residual acetic anhydride. This crude material, when dry, is dissolved in the minimum of hot ethyl acetate and allowed to crystallize overnight at 0° C. After filtering and washing with a little cold hexane, and drying in vacuo, the product weighed about 150 g and has a melting point of about 112°–113° C.

EXAMPLE D

6-chloro-N-acetylindol-3-ol

A solution of 572 ml of concentrated sulfuric acid is added to 63 ml of water with stirring and cooling. When the acid solution is at room temperature, 134 g (0.53M) of 6-chloroindoxyl-1,3-diacetate is added, portionwise, with stirring over a period of one hour keeping the temperature of the solution between 20° C. and 25° C. After stirring for 30 additional minutes after the addition is complete, the solution is poured onto 2 kilograms of ice. The ice is allowed to melt and the insoluble product is recovered by filtration and washed with cold water. This product is then protected from light and air and dried in a vacuum oven at room temperature. The yield of light yellow solid is about 110 g. This product is very unstable and may not be stored for long periods without decomposition. It is used immediately in the next step.

The following Examples 1 to 4 illustrate the preparations of chromogenic 6-chloro-3-indolyl compounds of the present invention.

EXAMPLE 1

6-chloro-3-indolyl phosphate p-toluidine salt

In a 500 ml 3-neck flask with nitrogen purge, drying tube and stirrer is added 250 ml of dry pyridine. To this is added 10 g (0.0477 mole) of 1-acetyl-6-chloro-indol-3-ol. The flask is cooled to less than about 10° C. in a methanol/dry ice bath in a darkened hood. To the suspension is added 5.5 ml of phosphorous oxychloride. The temperature is allowed to come up to 0° C. and maintained for 4 hours. The reaction mixture turns a light red color. The reaction mixture is allowed to stir overnight. The solution is rotovaped to dryness (less than about 50° C.) using a cold trap and vacuum pump. The resulting residue is taken up in 100 ml of ice cold water and adjusted to pH of 9.0 with 10% KOH. The dark solution is rotovaped to dryness and traces of water removed by 3 evaporations of 100 ml portions of ethanol. The resulting solid residue is dissolved in 100 ml of dry methanol. To this dark solution is added a 20 ml portion of dry methanol containing 1.6 g of potassium metal. This mixture is stirred overnight on a stirring plate. The mixture is neutralized with a small portion of acetic acid to a pH between 5.5 and 6.0. This solution is rotovaped to dryness. The residue is dissolved in 100 ml of water and charcoal filtered. A solution of 6.9 g of p-toluidine hydrochloride is prepared in 100 ml of water. The p-toluidine solution is stirred into the reaction solution. The resulting precipitate is collected by vacuum filtration, washed with ethanol and vacuum dried.

The dry product yielded 10.0 g of material. This is recrystallized from hot ethanol with charcoal filtering to obtain pure product. After drying, 4.2 g of pure material is obtained.

| Yield | 4.2 g | | |
|---|---|---|---|
| | C | H | N |
| Actual | 50.8 | 4.55 | 7.90 |

| Melting Point | 167–168° C. |
|---|---|
| TLC | Silica Gel: Solvent - 7:3 MeOH:H$_2$O |
| | Dissolve in 0.1 N NAOH |
| | One Spot   Rf = 0.9 |

EXAMPLE 2

Preparation of 6-chloro-3-indolyl acetate

A 45 ml solution of 2N NaOH is added to a multi-necked flask fitted with a heating mantle, stirrer, reflux condenser, addition funnel and delivery tube which reaches into the solution. A slow stream of oxygen free nitrogen is bubbled through the solution for 5 minutes. To the flask is added 2.52 grams (0.010 mole) of 6-chloro-1,3-indolyl diacetate. Stirring and nitrogen purge are continued for an additional five minutes. The mixture is heated to reflux until the 6-chloro-1,3-indoyl diacetate is completely dissolved. The solution is then allowed to cool to room temperature and then chilled in an ice bath to 0° C. Using the addition funnel, 5.3 ml of acetic anhydride is added dropwise to the solution with rapid stirring. After addition of acetic anhydride is completed, the solution is allowed to stir for an additional 20 minutes. The precipitated product is collected by vacuum filtration and washed with water. The crude product is dried in vacuo over P$_2$O$_5$.

The crude product is purified by recrystallization from ethanol using gentle heat. The solution is charcoal filtered to remove color. The solution is reheated and an equal volume of water at approximately the same temperature is added to precipitate product. After cooling, the product is collected by vacuum filtration using water to wash. The product is dried in vacuo over P$_2$O$_5$.

EXAMPLE 3

Preparation of 6-chloro-3-indolyl-$\beta$-D-glucopyranoside

A 250 ml 3-neck round bottom flask with mechanical stirrer, thermometer, nitrogen purge and addition funnel is set up in a dry ice-methanol bath. 65 ml of dry methanol is added to the flask and 0.60 g (0.026 mole) of sodium metal is dissolved in the methanol. The solution is cooled to about −5° C. and purged with nitrogen. To this solution is added 5.45 g (0.026 mole) of 6-chloro-3-indolyl acetate. Stirring and nitrogen purge are maintained for 30 minutes. A solution of 11.1 g (0.027 mole) of acetobromoglucose dissolved in 65 ml of dry methanol is added dropwise from the addition funnel while maintaining the temperature at about 0° C. After addition is complete, the temperature is allowed to reach room temperature and the solution is stirred for 18 hours. The resulting solution is evaporated to a viscous oil using a rotovap apparatus. Upon stirring with water, the oil solidifies to form a dark product. This product is collected by vacuum filtration. The filter cake is stabilized with cold acetone to remove coloration and refiltered to obtain an off-white product. Pure product is obtained by recrystallization from ethanol.

EXAMPLE 4

Preparation of 6-chloro-3-indolyl nucleoside phosphodiesters

The method represents a general procedure for the preparation of 6-chloro-3-indolyl nucleoside phosphodiesters. To a pyridine solution of N-acetyl-6- chloro-3-indolyl phosphodichloridate prepared from 272 mg (1.30 mmoles) of 6-chloro-N-acetylindol-3-ol and 0.13 ml (1.30 mmoles) of $POCl_3$ is added 400 mg (1.15 mmoles) of 3'-O-acetyl-5-bromodeoxyuridine in 10 ml of anhydrous pyridine. The mixture is stirred for 24 hours and treated with 20 ml of 7M $NH_4OH$. The solution is allowed to stir for an additional 24 hours. The reaction mixture is evaporated to dryness, diluted with 500 ml of water and filtered. The resulting flitrate is applied to a DEAE-Sephadex A-25 column ($HCO_3$ form) and eluted with a linear gradient of 4 liters each of 0.01M $NH_4HCO_3$ and 0.40M $NH_4HCO_3$. After the gradient, the column is eluted with 0.5M $NH_4HCO_3$. Fractions of 20 ml each which show the desired UV are pooled and lyophilized to give a powdered product.

The present invention further relates to a method for quantitatively identifying and differentiating a first biological material having enzyme specificity for a first chromogenic compound and a second biological material having enzyme specificity for a second chromogenic compound, comprising the steps of: combining the first chromogenic compound capable of forming an insoluble precipitate of a first color upon reacting with an enzyme from the first biological material, a second chromogenic compound capable of forming an insoluble precipitate of a second color contrasting with the first color upon reacting with an enzyme from the second biological material, and a nutrient base medium to form a test medium; inoculating the test medium with a sample to be tested for the presence of biological material; incubating the test medium, examining the test medium for the presence of colonies having the first color, such colonies being colonies of the first biological material having enzyme specificity for the first chromogenic compound, and the presence of colonies having the second color, such colonies being colonies of the second biological material having enzyme specificity for the second chromogenic compound; and enumerating the colonies of the first biological material and the colonies of the second biological material. The chromogenic compounds of the present invention enable the quantification, identification and/or differentiation of biological material having enzyme specificity for a particular $R_2$ group and biological material not having such enzymatic specificity. The enzymes may be naturally occurring or may be artificially introduced into biological material, such as a bacterium or a yeast by conventional genetic transfection techniques. Biological material, for purposes of the present invention, may be any material related to the fields of biotechnology, diagnostic chemistry, microbiology, molecular biology and the like. For example, biological material may include antibodies, antigens, DNA, RNA, cells, cell subparts, microorganisms, proteins and the like. Specifically, the chromogenic compounds of the present invention may be effective for quantifying, identifying and/or differentiating specific enzymes linked to an antibody, antigen, DNA or RNA sequences, nucleic acid probes, affinity proteins, matrixes, transfectants, microorganisms and the like.

The following is an example of a method for quantitatively identifying and differentiating a first biological material having enzyme specificity for a first chromogenic compound and a second biological material having enzyme specificity for a second chromogenic compound. The preparation of a test medium which may be suitable for use in this invention involves a chromogenic compound of the present invention and at least one other chromogenic compound, which does not produce an approximate magenta color.

To prepare sufficient quantity of chromogenic compounds of the present invention and other chromogenic compounds for one liter of medium, 150 mg of a first chromogenic compound of the present invention, and 75 mg of a second chromogenic compound not of the present invention, are weighed and added to 5 ml of dimethylformamide. The mixture is agitated until dissolved. An additional 10 ml of deionized water is added and mixed. The mixture is filtered sterilized with a micropore filter.

The test medium is formed by combining the chromogenic compounds with a nutrient base medium. The nutrient base medium can be any culture medium known in the art for growing biological material, such as microorganisms. Generally such media include growth nutrients, buffers, water, and a gelling agent. Possible gelling agents include agars, pectins, carrageenans, alginates, locust bean, and xanthins, among others.

Standard agar medium may be made by adding 15 g of bacteriological quality agar gum to the following nutrient formula:
Pancreatic Digest of Casein—5.0 g
Yeast Extract—3.0 g
Dipotassium Phosphate—0.3 g
Deionized Water—1000 ml
and then sterilizing at 121° C. for 15 minutes. The medium should be adjusted to result in a pH of 7.0. The sterilized agar medium is allowed to drop to a temperature of 45° C. in a water bath and then a sterile solution containing 150 mg of the first chromogenic compound and 75 mg of the second chromogenic compound are added. The medium is mixed thoroughly and poured into sterile petri plates at a volume of 20 ml/plate.

A pectin-based test medium may be prepared using the same steps described above except that 25 gm of low methoxyl pectin is used as the solidifying agent and the medium is poured at room temperature into petri plates containing a thin gel layer containing calcium ions which combine with the pectin to form a solid gel. A suitable pectin culture medium is described in U.S. Pat. Nos. 4,241,186 and 4,282,317, the disclosures of which are incorporated herein by reference. A pectin-based medium is often preferred over a standard agar medium because it has the advantages of convenience and temperature independence for the user. A suitable pectin medium is commercially available from Conviron, Inc. under the trademark Redigel.

The test medium may be inoculated, with a sample to be tested for the presence of a first biological material having enzyme specificity for the first chromogenic compound of the present invention and a second biological material having enzyme specificity for the second chromogenic compound capable of forming an insoluble precipitate of a color other than magenta, by any method known in the art for inoculating a medium with a sample containing biological material. For example, the sample to be tested may be added to the petri plates prior to adding the nutrient base medium (pour plate technique) or spread on the surface of the plates after they have cooled and solidified (swab or streak plate technique).

The inoculated test medium is incubated for a sufficient time and at such a temperature for the biological materials present in the sample to grow into detectable colonies. Suitable incubation conditions for growing various biological materials in a medium are known in the art. Preferably, the test medium is incubated for about 24–48 hours at a temperature of about 30°–40° C.

The first biological material produces an enzyme which acts upon the first chromogenic compound (of the present invention) in the test medium, causing the first chromogenic compound to form an insoluble, magenta precipitate. Because the precipitate is insoluble in the test medium, it remains in the immediate vicinity of the first biological material. The second biological material produces an enzyme which acts upon the second chromogenic compound (not of the present invention) in the test medium, causing the second chromogenic compound to form an insoluble precipitate of a color other than magenta, such as blue. The colonies of the first biological material show as colonies having a color different from and contrasting with the color of the second biological material because of the contrastingly colored insoluble precipitates. Generally, the second chromogenic compound contains a 5-bromo-4-chloro-3-indolyl, 5-bromoindolyl or 3-indoxyl substituent. Preferably, the second chromogenic compound is 5-bromo-4-chloro-3-indolyl-$\beta$-D-galactopyranoside or 5-bromo-4-chloro-3-indolyl-$\beta$-D-glucuronic acid.

Since the first chromogenic compound (of the present invention) and the second chromogenic compound are selected so that the colors of the precipitate produced by each contrast with each other, the colonies of each type of biological material can be readily differentiated by visual means. For example, if 6-chloro-3-indolyl-$\beta$-D-glucopyranoside is used as the first chromogenic compound and 5-bromo-4-chloro-3-indolyl-$\beta$-D-glucuronide is used as the second chromogenic compound, the first biological material will shown as magenta-colored colonies and the second biological material as indigo blue-colored colonies.

The colonies of each type of biological material may be enumerated by counting the colonies or by other methods known in the art. The number of colonies of each type indicates the amount of biological material of each type originally present in the sample before incubation.

The methods of the present invention does not require inhibitors. However, the medium may be made more selective for some biological material if desired by the addition of various compounds that are inhibitory to certain biological material not of interest, but have little or no effect on the biological material being tested. Following are some compounds which may be used when testing coliforms or E. coli: a) Bile Salts, about 0.3 g/liter, b) Sodium Lauryl Sulfate, about 0.2 g/liter, c) Sodium desoxycholate, about 0.2 g/liter, d) Tergitol 7, about 0.1 ml/liter. The use of one or more of these compounds reduces the background (non-coliform) microorganism presence and makes a less cluttered plate and eliminates the possibility of inhibition or interference by the non-coliform organisms in the sample.

It is possible that the enzyme production of the biological material may be enhanced by the addition to the medium formulations of very small amounts of substances known as enzyme inducers. For example, the specific inducer for $\beta$-galactosidase is available and is known chemically as isopropyl-$\beta$-D-thiogalactopyranoside. Adding approximately 25 mg/liter of medium has a positive and noticeable effect on the speed of enzyme production for some species of coliforms.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A chromogenic compound having Formula (I):

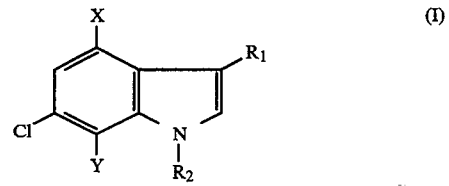

wherein $R_1$ is a sugar group, propionate group, butyrate group, hexanoate group, octanoate group, hydrocarbyl group containing 1 to about 10 carbon atoms, phosphate group, sulfate group or a salt thereof, with the proviso that $R_1$ is other than $\beta$-D-glucuronic acid or $\beta$-D-galactopyranoside, $R_2$ is H or hydrocarbyl group containing 1 to about 5 carbon atoms, X is Cl or H, and Y is Cl or H.

2. The chromogenic compound of claim 1 wherein $R_2$ is a hydrocarbyl group containing 1 to about 5 carbon atoms.

3. The chromogenic compound of claim 1 wherein $R_1$ is an ester group selected from the group consisting of propionate, butyrate, hexanoate and octanoate.

4. The chromogenic compound of claim 1 wherein $R_1$ is a sugar group or a salt thereof.

5. The chromogenic compound of claim 4 wherein $R_2$ is a hydrocarbyl group containing 1 to about 5 carbon atoms.

6. The chromogenic compound of claim 1 wherein $R_1$ is a sugar group selected from the group consisting of $\beta$-D-galactosaminide, $\beta$-D-glucopyranoside, and $\beta$-D-glucosaminide.

7. The chromogenic compound of claim 1 wherein $R_1$ is a phosphate group or a salt thereof.

8. The chromogenic compound of claim 1 wherein $R_1$ is a phosphate derivative selected from the group consisting of pyrophosphates, nucleoside pyrophosphates, nucleoside phosphodiesters and salts thereof.

9. The chromogenic compound of claim 1 wherein $R_1$ is a sulfate group or a salt thereof.

10. The chromogenic compound of claim 1 wherein $R_1$ is a sulfate derivative or a salt thereof.

11. The chromogenic compound of claim 1 wherein $R_1$ is a nucleoside phosphodiester derivative or a salt thereof.

12. The chromogenic compound of claim 1 wherein Formula (I) is 6-chloro-3-indolyl-N-acetyl-$\beta$-D-galactosaminide.

13. The chromogenic compound of claim 1 wherein Formula (I) is 6-chloro-3-indolyl-N-acetyl-$\beta$-D-glucosaminide.

14. The chromogenic compound of claim 1 wherein Formula (I) is 6-chloro-3-indolyl butyrate.

15. The chromogenic compound of claim 1 wherein Formula (I) is 6-chloro-3-indolyl octanoate.

16. The chromogenic compound of claim 1 wherein Formula (I) is 6-chloro-3-indolyl phosphate p-toluidine salt.

17. The chromogenic compound of claim 1 wherein Formula (I) is 6-chloro-3-indolyl sulfate.

18. The chromogenic compound of claim 1 wherein Formula (I) is 6-chloro-3-indolyl-β-D-glucopyranoside.

19. A chromogenic compound having Formula (II):

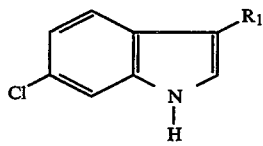

(II)

wherein $R_1$ is a sugar group, propionate group, butyrate group, hexanoate group, octanoate group, hydrocarbyl group containing 1 to about 10 carbon atoms, phosphate group, sulfate group or a salt thereof, with the proviso that $R_1$ is other than β-D-glucuronic acid or β-D-galactopyranoside.

20. The chromogenic compound of claim 10 wherein $R_1$ is a phosphate group or a salt thereof.

21. The chromogenic compound of claim 19 wherein $R_1$ is a sugar group or a salt thereof.

22. The chromogenic compound of claim 19 wherein $R_1$ is a ester group selected from the group consisting of propionate, butyrate, hexanoate and octanoate.

23. The chromogenic compound of claim 19 wherein $R_1$ is a sulfate group or a salt thereof.

24. The chromogenic compound of claim 19 wherein $R_1$ is a sugar group selected from the group consisting of β-D-galactosaminide, β-D-glucopyranoside, and β-D-glucosaminide.

25. The chromogenic compound of claim 19 wherein $R_1$ is glucopyranose.

26. A method for quantitatively identifying and differentiating a first biological material having enzyme specificity for a first chromogenic compound having Formula (I):

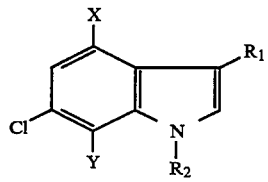

(I)

wherein $R_1$ is a sugar group, propionate group, butyrate group, hexanoate group, octanoate group, hydrocarbyl group containing 1 to about 10 carbon atoms, phosphate group, sulfate group or a salt thereof, with the proviso that $R_1$ is other than β-D-glucuronic acid or β-D-galactopyranoside, $R_2$ is H or hydrocarbyl group containing 1 to about 5 carbon atoms, X is Cl or H, and Y is Cl or H and a second biological material having enzyme specificity for a second chromogenic compound, comprising the steps of:

combining said first chromogenic compound capable of forming an insoluble precipitate of a first color upon reacting with an enzyme from said first biological material, a second chromogenic compound capable of forming an insoluble precipitate of a second color contrasting with said first color upon reacting with an enzyme from said second biological material, and a nutrient base medium to form a test medium;

inoculating said test medium with a sample to be tested for the presence of biological material;

incubating the inoculated test medium;

examining the incubated test medium for the presence of colonies having said first color, such colonies being colonies of said first biological material having enzyme specificity for said first chromogenic compound, and the presence of colonies having said second color, such colonies being colonies of said second biological material having enzyme specificity for said second chromogenic compound; and enumerating said colonies of said first biological material and said colonies of said second biological material.

* * * * *